United States Patent [19]

Collins

[11] 4,250,753

[45] Feb. 17, 1981

[54] MOLTEN MATERIAL SAMPLER

[76] Inventor: William J. Collins, 7005 Madison St., Merrillville, Ind. 46410

[21] Appl. No.: 52,455

[22] Filed: Jun. 27, 1979

Related U.S. Application Data

[63] Continuation of Ser. No. 855,366, Nov. 28, 1977, abandoned.

[51] Int. Cl.³ ............................................. G01N 1/12
[52] U.S. Cl. ............................ 73/425.4 R; 73/DIG. 9
[58] Field of Search ..................... 73/425.4 R, DIG. 9

[56] References Cited

U.S. PATENT DOCUMENTS

| | | | |
|---|---|---|---|
| 3,369,406 | 2/1968 | Lowdermilk | 73/DIG. 9 X |
| 3,584,511 | 6/1971 | Collins | 73/DIG. 9 X |
| 3,693,449 | 9/1972 | Collins | 73/DIG. 9 X |
| 3,753,372 | 8/1973 | Collins | 73/DIG. 9 X |
| 3,877,309 | 4/1975 | Hance | 73/DIG. 9 X |
| 3,897,689 | 8/1975 | Boron | 73/DIG. 9 X |
| 3,994,172 | 11/1976 | Kelsey | 73/DIG. 9 X |
| 4,002,073 | 1/1977 | Collins | 73/DIG. 9 X |
| 4,007,640 | 2/1977 | Boron | 73/DIG. 9 X |

*Primary Examiner*—John Petrakes
*Assistant Examiner*—Joseph W. Roskos
*Attorney, Agent, or Firm*—Charles S. Penfold

[57] ABSTRACT

The invention involves providing an elongated structure or unit for obtaining a sample of molten material from a supply thereof and in which its rear extremity is designed and constructed to provide an elongated tapered formation for slidably accommodating a lance whereby to facilitate manipulation of the unit for entry into the supply of molten material.

16 Claims, 8 Drawing Figures

MOLTEN MATERIAL SAMPLER

This application is a continuation of application Ser. No. 855,366 filed Nov. 28, 1977, now abandoned.

OBJECTIVES

One of the important objects of the invention is to provide an elongated structure or unit which comprises an outer housing, an inner elongated casing having a front extremity for supporting a device for receiving a sample of molten material and a rear extremity which is disposed in a complementary relationship to the housing to provide an elongated tapered formation for slidably accommodating a lance.

More particularly, the object is to locate the elongated casing, above referred to, so that its longitudinal axis is disposed at an acute angle with reference to the longitudinal axis of the outer housing, whereby portions of the casing in combination with portions of the housing define a tapered formation so that an end of a lance can be forcibly entered into the formation to obtain a relatively firm connection sufficient to manipulate the unit without accidentally releasing the latter. Due to this taper, lances having variable cross-sectional dimensions, within practical limits, can be readily cammed into the formation to establish a firm but detachable connection therebetween.

A significant objective of the invention is to provide a structure which can be readily utilized to obtain a sample of molten material from a supply thereof whether the latter is contained in a vessel or is substantially a flowing horizontal or vertical stream.

Another object is to provide a unit of the character described above in which an entrance tube for initially receiving a sample of molten material from a supply thereof, and which constitutes a component of the device, is so inclined or angularly disposed that a sample may more readily be obtained from a falling or running supply of molten material, as compared to a setup in which such a tube is located on the longitudinal axis of such an outer housing.

Also, an object is to so shape the pairs of portions so that they preferably form a housing and a casing which are multi-sided or substantially rectangular in cross-section so as to promote assembly of the members and minimize the profile of the unit whereby to facilitate safe penetration of the unit into the molten material.

Additional objects and advantages of the invention will become apparent after the description hereinafter set forth is considered in conjunction with drawings annexed hereto.

DRAWINGS

DESCRIPTION

Figure 1:
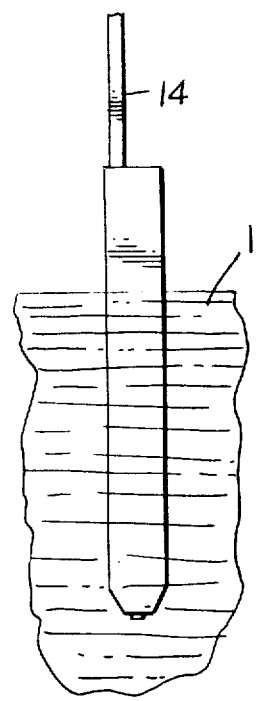
FIG. 1 is a partial view of a mass of molten material and structure embodying the invention, which is positioned in the mass for obtaining a sample therefrom.
Figure 2:
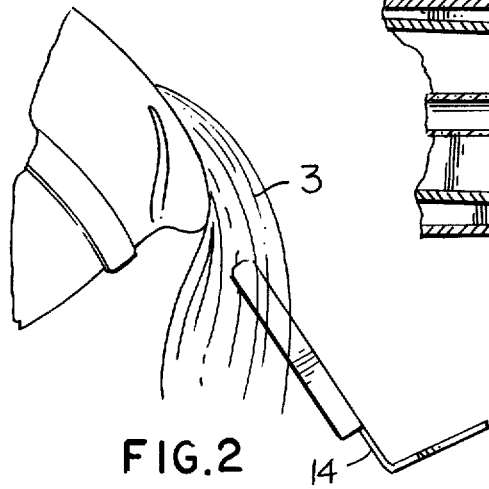
FIG. 2 is a partial view of downstream mass of molten material and depicts the structure positioned therein to obtain a sample therefrom.

The structure of the subject invention is adapted for use in obtaining a sample of molten metal from a molten mass 1 or from a downstream 3 as respectively illustrated in FIGS. 1 and 2, or from a horizontal stream.

FIGS. 3, 5, 6 and 7 disclose details of structure which comprises, among other things, an elongated outer housing 4, an inner casing 5, a pair of mating sections 6, at least partially held together by a band of tape T, to form a mold having a chamber or cavity 7 for receiving a sample of molten material through a tubular means 8 which has an inner extremity secured in a tubular formation 9 formed by the sections and an outer extremity which initially receives the sample for flow into the chamber 7 for solidification therein.

The structure also includes a partition or wall 10, preferably constructed of a fibrous material, such as pasteboard, which preferably abuts the fore end of the casing 5 and a mass of refractory or high density insulating material 11 which is molded into the housing 4 and against the partition 10 and about that portion of the tubular means 8 which extends forwardly of this partition. It will be noted that a cap 12 is press-fitted or otherwise secured about the fore end of the means 8 for protective purposes, when for example, the structure is utilized as depicted in FIG. 1. The cap is not used when the structure is employed as depicted in FIG. 2.

Attention is directed to the fact that the casing 5 is elongated, preferably disposed in the housing throughout the length of the area in back of the partition 10, and that it is arranged in an inclined or angular position with respect to the longitudinal axis of the housing so that lower portions of the casing and housing, in combination, provide an elongated tapered formation or area 13 for slidably accommodating a fore end of a lance 14. This taper offers a snug and firm fit for the lance and allows for the reception of lances which may have variable cross-sectional dimensions.

Attention is also directed to the fact, that the housing, casing and partition are multi-sided and preferably constructed of a suitable non-metallic material, such as pasteboard or equivalent, and that side walls of the casing 5 are preferably respectively provided with abutment means in the form of staples 15 (one shown), whereby to afford stop means for limiting inward movement of the mold; and that the partition 10 and mass 11 limit forward movement of the casing and mold, the latter two of which constitute a unit or subassembly of the structure.

Figure 4:
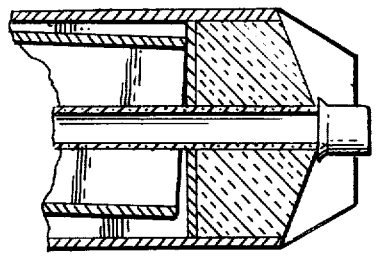
FIG. 4 is a partial view of a modified structure.
Figure 3:
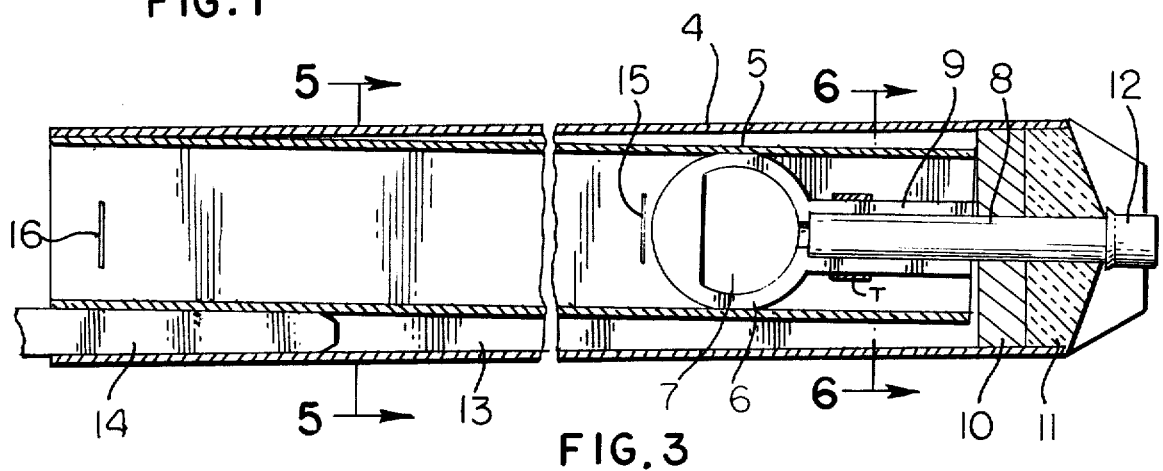
FIG. 3 is a horizontal section taken on the structure shown in FIG. 1 and 2.

It is to be understood, that, if found desirable, the thickness of the partition 10 may be modified to a reduced thickness as shown in FIG. 4 or it can be omitted, in which event, certain of the spaces or voids about the mold may be filled with a mass of refractory material.

Also, it is to be understood that the casing 5 has cross-dimensions which are less than the internal cross-dimensions of the outer housing so that the casing may be readily manually inserted into the housing to obtain a relatively snug frictional fit therebetween and that, if so desired, the casing may be located so that its upper portions and upper portions of the housing in combination, form an upper tapered formation for accommodating a lance, in lieu of the lower one shown.

The housing and casing, as set forth above, are preferably of a multi-sided character but if so desired they may, for example, be round or oval in cross section. Further, if found desirable, the formation for accommodating a lance may be fashioned in any suitable way so long as the fit is sufficient to provide a firm but detachable connection between the structure and lance. Obviously, the cross-sectional dimensions and/or configurations of a lance may be modified and a lance may be made straight as shown in FIG. 1 or angled as depicted in FIG. 2.

The casing 5, as alluded to above, is of appreciable length and it serves as a vent or flue for the escape of air from the mold when it is receiving a sample from a mass of molten metal. This casing may be secured in place and to the housing by any means suitable for the purpose such as by staples 16 and the partition 10 and mass 11 through the agency of the tubular means 8 but, if so desired, a cement may be used.

Figures 6, 7:
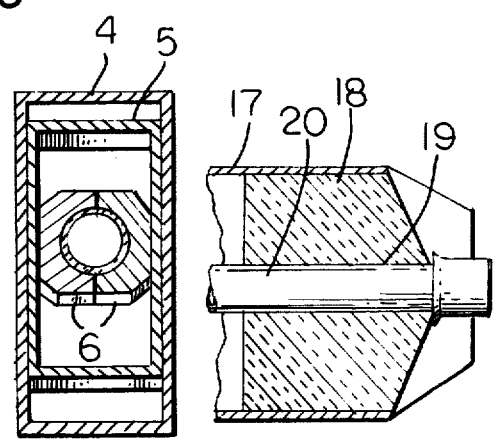
FIG. 6 is a transverse section taken substantially on line 6—6 of FIG. 3.
FIG. 7 is a partial horizontal section of a modified structure.

FIG. 7 depicts a partial section of a structure having a housing 17 in which a partition is omitted and a mass 18 preformed refractory material has been press fitted into the housing, in which event, the mass is provided with an axial opening 19 for slidably receiving a tubular means 20.

Figure 8:
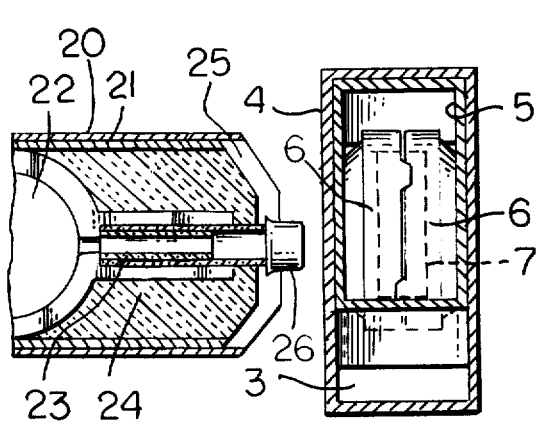
FIG. 8 is a partial horizontal section of another modified structure.
Figure 5:
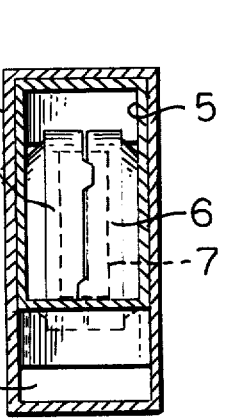
FIG. 5 is a transverse section taken substantially on line 5—5 of FIG. 3.

FIG. 8 is a partial section of structure showing an outer housing 20, an inner casing 21 containing a device 22 having a chamber for receiving a sample of molten material through a tubular means 23 connected thereto which extends forwardly for initially receiving the molten material for flow into the chamber. The improvement comprises filling the force extremity of the casing with a mass of refractory material 24 so that it surrounds at least frontal portions of the device whereby to at least partially hold or stabilize the position of the device. The housing has forwardly extending portions 25 which more or less substantially straddle a portion of the tubular means 23 and a cap 26 carried thereby for protective purposes.

SUMMARY

In view of the foregoing it should be manifest that the improvement constituting the subject invention primarily resides in providing wall structure which forms an outer housing having a front area which is adapted to receive a device for obtaining a sample of molten material, and that means is disposed in a rear area of the housing which forms in combination therewith an elongated formation for slidably accommodating a fore end of a lance whereby to facilitate manipulation of the structure into a supply of molten material for obtaining a sample thereform.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. Means for connecting a lance and a device for obtaining a sample of hot liquid, said connecting means comprising wall structure forming an outer elongated housing structure, an inner casing fixedly secured in said housing structure for receiving such a device and forming in combination with said housing structure an elongated formation having an inclined surface for slidably accommodating an end of a lance.

2. Means for affording connection of a lance to a device for determining a condition of molten material, said connection means comprising wall structure forming an outer housing for containing such a device, and means fixedly secured in said housing and forming in combination therewith a formation having an inclined surface for slidably accommodating an end of a lance.

3. In combination: an outer elongated housing, a device mounted in one extremity of said housing for receiving a sample of a hot liquid, and wall structure fixedly securely in its opposite extremity and forming in combination therewith an elongated formation having an inclined surface for slidably accommodating an end of a lance.

4. Structure of the character described comprising an elongated outer housing provided with a partition dividing it into a relatively short front compartment and a relatively long rear compartment, an elongated casing disposed in said rear compartment at an angle with respect to a longitudinal axis of said housing, means disposed in said casing for receiving a sample of a hot liquid, tubular means disposed in said front compartment and communicating with said receiving means through said partition for initially receiving a sample from a supply of such a liquid, and means disposed in said front compartment surrounding said tubular means for stabilizing its position.

5. Structure comprising an elongated housing, an elongated casing disposed in said housing at an angle with reference to its longitudinal axis, means in a fore extremity of said casing having a chamber for receiving a sample of molten material, tubular means communicating with said chamber and having a forwardly extending extremity for initially receiving a sample of such a material for flow into said chamber, and a mass of refractory material disposed in said housing and substantially surrounding said extending extremity of said tubular means.

6. The structure defined in claim 5, in which a partition is interposed between said casing and said mass of refractory material.

7. The structure defined in claim 5, in which at least a portion of said extending extremity of said tubular means is angularly disposed.

8. The structure defined in claim 5, including abutment means carried by said casing for limiting rear movement of said receiving means therein.

9. The structure defined in claim 8, in which said housing and casing are of a multi-sided character.

10. The structure defined in claim 5, in which portions of said housing project forwardly in substantially straddling relation to said extending portion of said tubular means.

11. A subassembly for use with means for obtaining a sample of molten material, said subassembly comprising multi-planar wall structure forming an elongated housing, a mass of refractory material secured in a fore extremity of said housing and provided with an opening through which a tube may be extended, and said wall structure having forwardly extending planar portions for protecting such a tube when it is correctly positioned in said opening for initially receiving such a sample and portions fixedly secured in a rear extremity of said housing and forming in combination therewith an elongated formation having an inclined surface for slidably engaging an end of a lance.

12. A subassembly for the purpose described comprising an elongated outer housing, an inner casing received in a frontal area of said housing, a device disposed in said casing and having a chamber for receiving a sample of molten material, tubular means extending from said device and having an outer entrance for initially receiving material for flow into said chamber, a mass of high density material disposed in said casing and about portions of said device, and means disposed in a rear area of said housing and forming therewith an inclined surface for engaging a lance.

13. Means for connecting a lance and a device for obtaining a sample of molten material, said connecting means comprising wall structure forming an outer elongated housing having a longitudinal wall, an inner casing of appreciable length secured in said outer housing for receiving such a device and having a longitudinal portion spaced from and opposite said longitudinal wall providing in combination therewith a formation for slidably accommodating an end of a lance whereby to assist in holding the latter in said formation.

14. A subassembly for the purpose described comprising an elongated casing for use in an elongated outer housing, said casing having a fore extremity for supporting a device for obtaining a sample of molten material, and said casing having a rear extremity provided with a longitudinally extending planar portion for engaging planar a lance whereby to assist in holding the latter thereto.

15. The subassembly defined in claim 14, including a mass of insulating material secured in said fore extremity so that a portion of said material extends forwardly of said casing to form a tapered formation, and an entrance tube extending axially through said formation for receiving such a molten material for flow into such a device.

16. In combination: an elongated outer housing, an elongated inner casing secured in said outer housing and extending throughout the major length of said housing, said casing having a fore extremity for supporting means for obtaining a sample of molten material, and said casing having a rear extremity provided with a longitudinal portion which is spaced inwardly from an inner surface of said housing to define in combination therewith an elongated formation for receiving a lance.

* * * * *